United States Patent [19]
Keller, Jr. et al.

[11] 4,203,447
[45] May 20, 1980

[54] SECURITY MAINTENANCE FOR PROGRAMMABLE PACER REPROGRAMMING

[75] Inventors: John W. Keller, Jr., Miami, Fla.; Dennis Digby, Brooklyn Park; Alan Coombes, New Hope, both of Minn.

[73] Assignee: Biotronik Mess-und Therapiegeräte GmbH & Co., Berlin, Fed. Rep. of Germany

[21] Appl. No.: 917,130

[22] Filed: Jun. 19, 1978

[30] Foreign Application Priority Data

Aug. 19, 1977 [GB] United Kingdom ............... 34911/77

[51] Int. Cl.² ............................................. A61N 1/36
[52] U.S. Cl. ............................................. 128/419 PG
[58] Field of Search ................................ 128/419 PG

[56] References Cited

U.S. PATENT DOCUMENTS

| | | | |
|---|---|---|---|
| 3,805,796 | 4/1974 | Terry, Jr. et al. | 128/419 PG |
| 3,833,005 | 9/1974 | Wingrove | 128/419 PG |
| 3,906,348 | 9/1975 | Willmott | 325/37 |
| 3,945,387 | 3/1976 | Adams | 128/419 PG |
| 4,049,004 | 9/1977 | Walters | 128/419 PG |
| 4,124,031 | 11/1978 | Mensink et al. | 128/419 PG |
| 4,126,139 | 11/1978 | Walters et al. | 128/419 PG |

FOREIGN PATENT DOCUMENTS 2030474 1/1971 Fed. Rep. of Germany.
76880 3/1971 Luxembourg.

*Primary Examiner*—William E. Kamm
*Attorney, Agent, or Firm*—Spencer & Kaye

[57] ABSTRACT

A counter functions in response to an oscillator to control generation of stimulating pulses in the demand mode, via an adjustable rate decoder. The rate decoder may be predetermined under the control of a dual input, a first of which is a magnetic enabling switch, and the second of which is a pulse width modulated magnetic transmission. Once the enabling switch is actuated, plural successive reprogramming bits are coupled to the pacer. Integral logic allows these bits actually to accomplish the programming alteration if and only if the predetermined number of bits occur during a predetermined interval. The reprogramming is further synchronized with the generation of stimulating pulses.

13 Claims, 2 Drawing Figures

SECURITY MAINTENANCE FOR PROGRAMMABLE PACER REPROGRAMMING

TECHNICAL FIELD

This invention relates to implantable body function control apparatus and particularly, but not exclusively, to body tissue stimulating devices such as cardiac pacemakers.

BACKGROUND ART

Pacemakers for generating artificial stimulating pulses for the heart, and which may be implanted in the body, are well known. Originally the electrical circuitry for such pacemakers was of analog design, but in recent years digital circuitry has also been employed. A digital approach to pacemakers has led to the evolution of programmable pacemakers—pacemakers having paramaters such as pulse rates which are adjustable (programmable) once the pacemaker has been implanted. Programmable pacemakers are described in, for instance, British Specification Nos. 1,385,954 and 1,398,875. Such pacemakers have circuitry to detect and decode signals transmitted outside the body and alter the program accordingly. In British Specification No. 1,385,954 (claiming priority based on U.S. Ser. No. 141,694, in turn a parent of U.S. Pat. No. 3,805,796 to Tenz) the programming is accomplished by means of a magnetic field which is sensed by a magnetic reed switch; the opening and closing of the switch provides programming pulses to a program store. In British Specification No. 1,398,875 (based on U.S. Pat. No. 3,833,005 to Wingrove) the programming is by means of radio freuency transmission and reception.

It is clearly of paramount importance that the stored program in such equipment is only altered when desired and not, for example, in response to electrical noise generated in proximity to the pacemaker. If the pacemaker is arranged to receive and decode radio frequency signals for changing the stored program then clearly precautions must be taken to avoid any undesired radio frequency transmissions from altering the program.

DISCLOSURE OF INVENTION

The present invention relates to programmable implantable body function control apparatus which includes several advantages from the point of view of security for retaining the stored program and for only changing the stored program when desired. The apparatus provides a high degree of protection against the capability of noise changing the program.

According to the invention there is provided a programmable, implantable body function control apparatus having a control means for influencing a function of the body, means for changing at least one characteristic of the controlling influence, a program store for storing a predetermined number of program bits, the values of which are arranged to control said changing means, program detection means for detecting data signals and for decoding said signals to provide bits for the program store, and program change enable means which permits the decoded signals to be entered into the program store to replace the program therein only when the number of bits decoded from the data signals equals the predetermined number of program bits of the program store and only when such predetermined number of program bits has been decoded by the program detection means within a given period of time.

The apparatus of the invention, by means of its program change enable means, thus includes circuitry which protects the program from being changed unless the correct number of data bits is transmitted to the implanted device within a predetermined period of time. If more or less program bits are received and decoded within the time allotted, then the program cannot be changed.

Preferably the data signals are purse width modulated. When appropriately decoded, the data signals are preferably retained in a temporary store and then transferred into the program store when the conditions for actuating the program change enable means have been fulfilled.

In a typical embodiment of the invention, the body function control apparatus is a body tissue stimulator, in which case the control means comprises a stimulation pulse generator. Typically, the apparatus is an implantable programmable cardiac pacemaker of the demand or non-demand type where a change of program can be used to change the characteristics of the pacer pulses, for example the pulse rate, pulse width, pulse height.

Pulse width modulated programming provides a greater number of distinct programs per programming time period with a similar instrumentation as employed with known instrumentation based upon pulse counting or reed switch closure techniques.

BRIEF DESCRIPTION OF THE DRAWINGS

A preferred embodiment of the invention is illustrated in the accompanying drawings, in which.

BEST MODE FOR CARRYING OUT THE INVENTION

Figure 1:
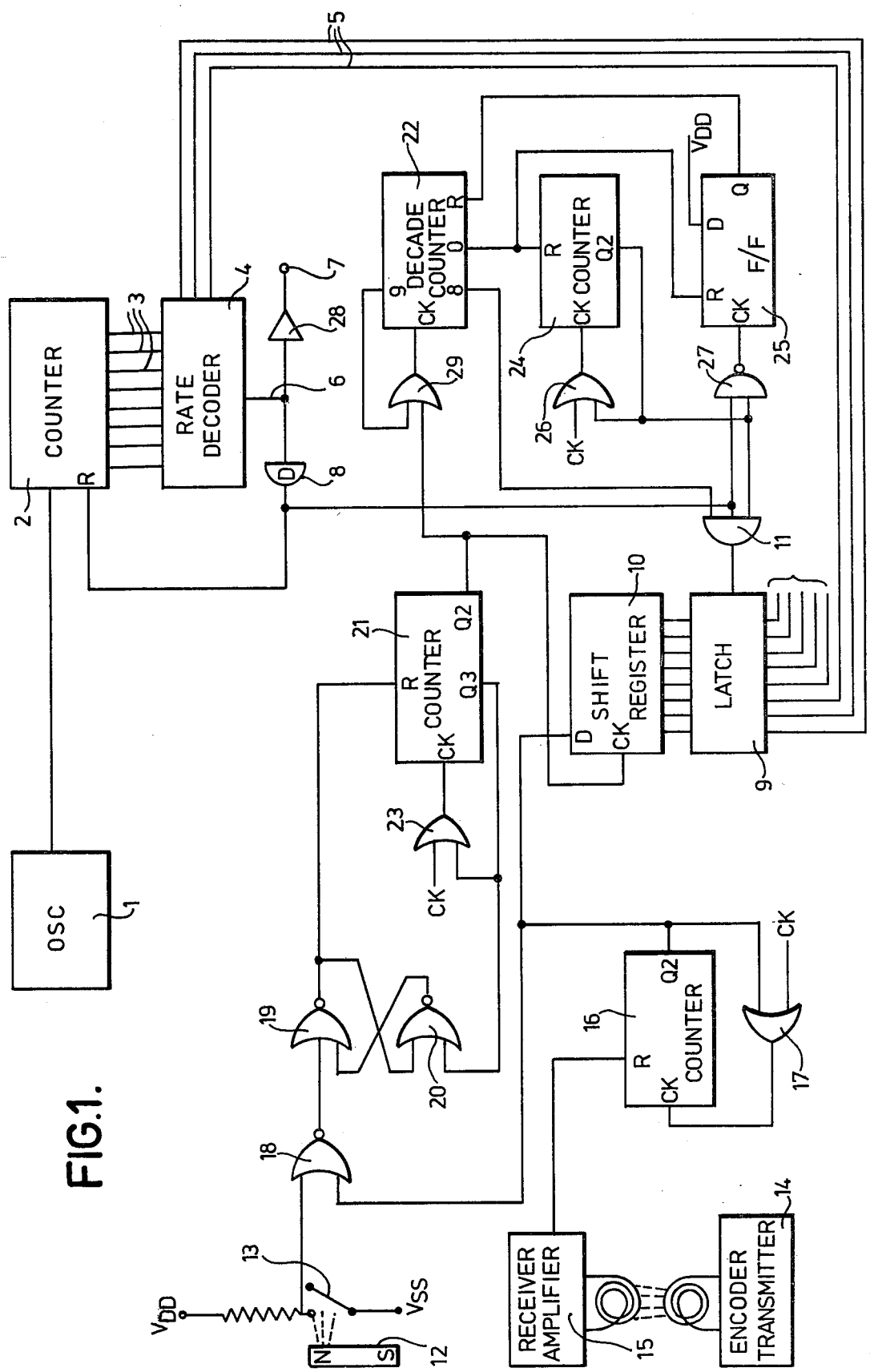
FIG. 1 represents schematically an electrical circuit diagram of the body function control apparatus when in the form of an implantable, programmable cardiac pacemaker.

Referring to the drawings, the pacemaker comprises an oscillator 1 which drives a ripple counter 2. The outputs of the various stages of the ripple counter are combined as is known in the art by means of logic gates (not shown) to provide eight output lines 3. The oscillator frequency and combination of ripple counter outputs are selected so that the eight output lines 3 provide, respectively, eight different body stimulation pulse frequencies (e.g. 40, 50, 60, 70, 80, 90, 100, and 110 pulses per minute). The eight output lines are supplied to a rate decoder 4 provided with three input control lines 5. By employing binary logic circuitry, the logic levels on the three lines 5 can be employed to select uniquely one from eight of the eight lines 3 and transmit the selected pulse frequency on line 6. Line 6 is connected via output amplifier 28 to an output terminal 7 and thence to a tissue stimulating pulse electrode disposed in or on the heart, and also to a delay unit 8 which, after an appropriate time, resets the counter 2, to enable the next appropriately timed pulse to be transmitted.

The bit values supplied on lines 5 to rate decoder 4 are obtained from an 8-bit latch 9 which stores a pacemaker program. As illustrated, three of the eight bits stored in latch 9 are employed to control the rate decoder 4 (i.e. the pulse rate) whereas the other five outputs from latch 9 are simply shown bracketed. These five outputs can be employed to control other pacemaker parameters as desired—e.g. pulse width, pulse height. The 8-bit latch values are set by corresponding values retained by a serial input/8-bit parallel output shift register 10. The shift register values are loaded into latch 9 upon receipt of a store signal to the latter from an AND gate 11.

The manner in which the program stored by latch 9 is changed is dependent upon a magnet 12 being held close to the body so as to close reed switch 13, coincidentally with the detection and transmission to the shift register 10 of tone burst modulated data signals (for changing the pacemaker program) from an encoder/transmitter 14 also located outside the body. The coincidence of these two conditions provides a defense against noise being detected by the apparatus as data signals for changing the program, and is more fully described in copending Applications Nos. 917,138, now abandoned and 917,139, both filed on June 19, 1978. For purposes of the presently-described embodiment "tone burst" modulation means pulse width modulation of a carrier frequency. The carrier is typically in the audio frequency range and with a sine wave modulator, but this need not be so and the invention is not so limited.

Encoder/transmitter 14 transmits tone burst modulated data signals to a receiver/amplifier 15, the output of which is employed to reset a counter 16. Counter 16 receives clock signals either from a system clock, advantageously 4 KHz., (e.g. from oscillator 1) or from its Q2 output stage, via an OR gate 17. The Q2 stage of counter 16 also drives the data input of shift register 10 and provides one input to NOR gate 18.

The second input to NOR gate 18 is derived from the normally high side of reed switch 13 which is connected between the electrical supply rails. NOR gate 18 output supplies one input to a pair of cross-coupled NOR gates 19, 20, with the output of NOR gate 19 being connected to the reset line of a ripple counter 21. Ripple counter 21 is such that the count pulses ripple successively through each of the counting stages—the lower stages do not remain high as the count proceeds to the higher stages. The Q2 output of ripple counter 21 is employed to clock shift register 10 and also a decade counter 22 via OR gate 29. The Q3 output of ripple counter 21 supplies one input to NOR gate 20 and to an OR gate 23. A second input to OR gate 23 is provided from a system clock, advantageously 250 Hz. (e.g. derived by subdividing clock pulses provided from oscillator 1) and the output of OR gate 23 is employed to clock ripple counter 21.

The zero stage of decade counter 22 is employed to reset a counter 24 and a flip-flop 25. The eighth stage of counter 22 provides one of three inputs to AND gate 11, and the ninth stage provides a return to OR gate 29 to lock out higher counts to counter 22. The reset line of the latter is driven by the Q output of the flip-flop 25.

Counter 24 is clocked via an OR gate 26 from a system clock, advantageously 4 H. (e.g. derived by subdividing clock pulses provided from oscillator 1). Its Q2 output stage provides a return to OR gate 26 to provide a disable function on the latter. The Q2 output of counter 24 also provides a second of the three inputs to AND gate 11, and also an input to a NAND gate 27 which drives the clock input of flip-flop 25. The D-input line of flip-flop 25 is tied to the positive supply rail $V_{DD}$.

The third of the three inputs to AND gate 11 receives the reset pulse for ripple counter 2, this latter pulse also being supplied to another input of NAND gate 27.

The manner in which the program stored by latch 9 is decoded and then changed by the above circuit will first be described generally, and then in more detail.

The Q2 stage of counter 21, by clocking shift register 10, defines the time at which the signals received by counter 16 are analyzed. Counter 21 effectively analyzes the state of the Q2 stage of counter 16 at predefined instants of time and clocks either the 0 or 1 present at that stage into the shift register.

The shift register 10 only transfers its content into the 8-bit latch 9, thereby changing the program, when the following three conditions are satisfied:

1. When eight (and only eight) data bits have been clocked into shift register 10 (i.e. eight clock pulses to counter 22). This prevents the program being changed if less than or more than eight data bits have been received.

2. At a predetermined time after the receipt of the first data bit. This sets a maximum time limit within which all eight data bits must be received. The program will not therefore change if, say, only seven bits are received and then, after some longer period of time, a further data bit is received. If such a circumstance occurs, the circuit treats the received bits as spurious and will not change the program.

3. When an instant of time exists when counter 2 is being reset. This condition causes the program to change only in synchronism with the pacing pulses being transmitted. The program does not thus change at an instant of time at an intermediate stage in a count produced by counter 2, since this might have the effect of causing the pacemaker to issue two pacing pulses in rapid succession or to leave a gap where a pacing pulse ought to have been issued.

The above three conditions are met by clocking the 8-bit latch 9 from AND gate 11, the three inputs of which supply the three conditions above-mentioned. These conditions therefore have to coincide before AND gate 11 is enabled so to clock the shift register 10 contents into the 8-bit latch 9.

Decade counter 22 counts the number of data bits clocked into shift register 10 and only provides a high input to AND gate 11 after receipt of the eighth data bit (condition 1). Counter 24 provides a high input to AND gate 11 a predetermined time after its reset is removed (from the zero output from decade counter 22) (i.e. from the time the first data pulse is received—condition 2). The third high input to AND gate 11 occurs when counter 2 is reset (condition 3).

The operation of the decoding and storage of data bit pulses will now be described in greater detail. Assume that initially the output Q2 of counter 16 is high, and that the reset line to counter 21 also is high. With no magnet 12 adjacent reed switch 13 the latter will be open, providing a high input to NOR gate 18. Assume also that decade counter 22 is reset to zero, thus holding a reset on counter 24 and flip-flop 25. Assume now that it is desired to change the program stored in 8-bit latch 9. A magnet 12 is placed in proximity to the body adjacent the site of the implanted pacemaker, thus closing switch 13 and providing a low input to NOR gate 18. Simultaneously with the magnet emplacement, eight data bits for changing the program are transmitted from encoder/transmitter 14 for receipt and amplification by receiver/amplifier 15. The latter transmits to the reset terminal of counter 16 eight tone bursts of about 10 KHz frequency. A long tone burst is employed as a wide data "pulse" for storing a "0" in the 8-bit latch whereas a short tone burst is employed as a narrow data "pulse" for storing a "1".

The receipt of the first tone burst resets counter 16 causing NOR gate 18 output to provide a high output to NOR gate 19 which therefore provides a low output. This removes the reset on counter 21 which thus commences counting clock pulses. The first tone burst pulse continues to reset counter 16 but eventually counter 21 counts to its Q2 stage, thus clocking shift register 10. This has the effect, at this instant, of "analyzing" the output of the Q2 stage of counter 16 and inserting its value into the shift register. If the first tone burst has been a long burst, it is arranged that counter 16 will still be being reset by the tone burst when the analysis time provided by the Q2 output of counter 21 arrives. In such a circumstance a zero exists at the Q2 stage of counter 16 and is clocked into the shift register 10.

If the first tone burst is short, it is arranged that it will be terminated, so that counter 16 is no longer being reset thereby and has counted to its Q2 stage, by the time the shift register is clocked by counter 21. In such a circumstance, a "1" is clocked into the shift register. Counter 16 will hold at the Q2 stage since its output is supplied via OR gate 17 to the clock input to lock out any further clock pulses.

In this manner, a long tone burst will cause a "0" to be clocked into the shift register, and a short burst will cause a "1" to be clocked into the shift register.

Figure 2:
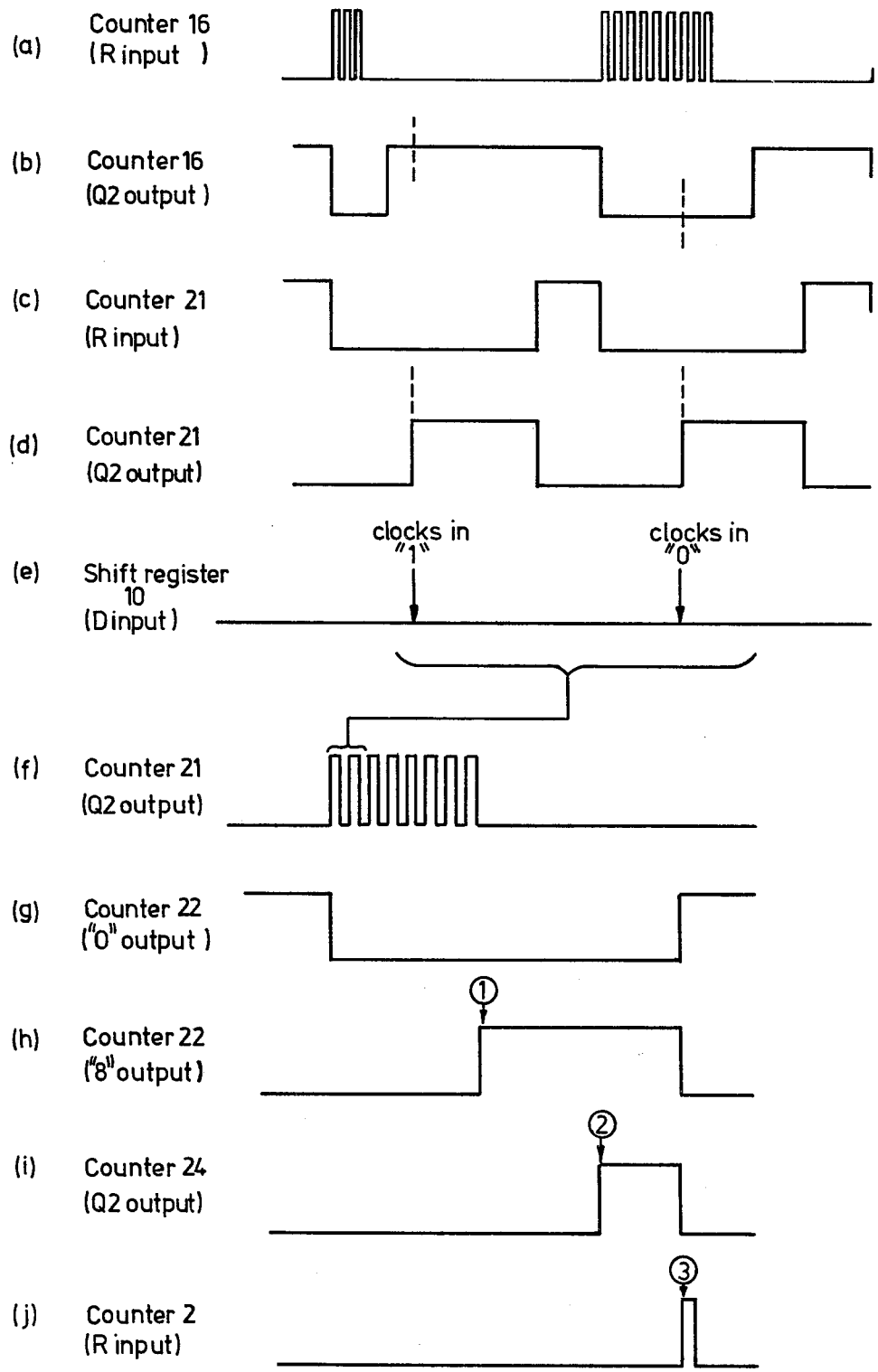
FIG. 2 represents a timing diagram for use in understanding FIG. 1.

In FIG. 2, the first tone burst illustrated is a short burst. The time at which the counter 21 analyzes the Q2 output of counter 16, for clocking the latter into the shift register, is shown by dashed vertical lines on pulse trains (b) and (d) in FIG. 2. This short tone burst thus causes a "1" to be stored in the shift register. The second tone burst illustrated in FIG. 2 is long, and this causes a "0" to be stored in the shift register.

Note also in FIG. 2 that pulse trains (f) to (j) are compressed in time as compared to pulse trains (a) to (e). Pulse trains (d) and (f) are identical except that the former shows schematically only two pulses whereas the latter shows eight pulses.

The Q2 high output of counter 21 also provides a clock pulse to decade counter 22 which thus counts the first data pulse now clocked in the shift register 10. After the arrival of two subsequent clock pulses to counter 21, the Q2 output goes low, and the Q3 output goes high to lock out further clock signals (via OR gate 23) until counter 21 is reset.

The clocking of decade counter 22 from zero to one removes the reset from counter 24, so that the latter commences counting clock pulses, and also removes the reset on flip-flop 25.

The locking of clock pulses provided by the Q2 stage on its counter 16, and the Q3 stage on its counter 21 causes a change in stages of the NOR gates 18, 19, 20 which causes the NOR gate 19 output to revert high, thus resetting counter 21.

This situation remains until the next tone burst pulse arrives at the reset input to counter 16, when the above-described cycle is repeated causing another data bit to be clocked into shift register 10 and decade counter 22 to increment by "1". In the meantime, counter 24 continues to count clock pulses.

This cycle repeats until all eight tone bursts are received, analyzed and the appropriate bits clocked into shift register 19, which then retains a complete new program for the pacemaker.

Decade counter 22 has then reached a count of 8 to provide the first of the three input conditions to AND gate 11. Counter 24, still counting clock pulses, then "times out" by providing a high output on its Q2 stage, which locks out further clock pulses via OR gate 26 and provides the second of the three input conditions to AND gate 11. As soon thereafter that the pacing pulse-producing counter 2 is reset, the third of the three input conditions to AND gate 11 is satisfied, the output of which then goes high to load the 8-bits retained in the shift register 10 into the 8-bit latch 9, thereby changing the stored program.

Coinciding with the presence of the second and third of the input conditions for AND gate 11, NAND gate 27 provides a low output of short duration (duration of counter 2 reset). The low to high transition at NAND gate 27 clocks flip-flop 25, causing the latter to reset decade counter 22 to zero, the latter causing counter 24 and flip-flop 25 to reset. The circuit is then in the condition to receive another set of eight tone bursts to change the program at some future occasion.

It should be observed that if less than 8 tone bursts are received before conditions 2 and 3 are met, the first of the three input conditions of AND gate 11 will not be satisfied. This situation will also arise if more thab 8 tone bursts are received before conditions 2 and 3 are met, since the ninth stage of decade counter 22 holds the clock input of the latter high to lock out any further clock pulses from counter 21. This holds counter 22 in the ninth stage until reset.

What is claimed is:

1. A programmable, implantable body function control apparatus comprising: control means for influencing a function of the body by providing a train of stimulation pulses in accordance with a selected program, said control means including means for changing the selected program in order to vary at least one parameter of the stimulation pulses; program storage means for storing a predetermined number of bits representing the currently selected program and connected to said means for changing for supplying the currently selected program to said control means; program detection means connected to receive and temporarily store a predetermined number of bits representing a newly selected program, said detection means including output means connected to said program storage means for supplying the bits received by said detection means; signal conduction means connected to receive bit signals provided by a source outside the body and to supply a corresponding sequence of bits, representing such newly selected program, to said program detection means in a pattern independent of that of the train of stimulation pulses being provided by said control means; and program change enable means connected to said program storage means for supplying a program change signal which causes the bits temporarily stored in said detection means to be transferred into said program storage means to replace the bits previously stored in said program storage means, said program change enable means being composed of: first counter means connected for providing a count of the number of bits supplied to said program detection means, and for supplying a first enabling signal only when its count is equal to, and does not exceed, the predetermined number of bits; timer means connected for responding to the first bit supplied to said program detection means and for supplying a second enabling signal at the end of a given period of time after response to such first bit;

synchronizing means connected to said control means for supplying a third enabling signal in synchronism with each stimulation pulse provided by said control means; and gating means connected to said counter means, said timer means and said synchronizing means for supplying such program change signal to said program storage means only when said first, second and third enabling signals are present in time coincidence, whereby the bits temporarily stored in said program detection means can be transferred into said program storage means only when precisely the predetermined number of bits has been supplied to said program detection means within the given period of time and at a point in time which is in synchronism with a stimulation pulse provided by said control means.

2. An apparatus according to claim 1 wherein the program detection means includes a temporary store in which the bits supplied by said conduction means are retained, said program change enable means transferring the bits from said temporary store into said program storage means only when a program change signal appears.

3. An apparatus according to claim 1 wherein the bit signals received by said conduction means are pulse width modulated.

4. An apparatus according to claim 3 wherein the bit signals received by said conduction means are tone burst modulated.

5. An apparatus according to claim 1 wherein said program storage means is a latch having capability for storage of said predetermined number of program bits.

6. An apparatus according to claim 1 when in the form of a body tissue stimulating apparatus and wherein said control means comprises a stimulation pulse generator.

7. An apparatus according to claim 6 wherein said pulse generator comprises an oscillator, and a second counter driven by said oscillator providing at least two different pulse rates, said changing means including a rate decoder whereby at least some of the program bits in said program storage means control said rate decoder to select one of the pulse rates provided by said second counter.

8. An apparatus according to claim 7 wherein the output pulse selected is arranged to reset said second counter.

9. An apparatus according to claim 8 wherein said synchronizing means is connected to provide said third enabling signal in time coincidence with resetting of said second counter.

10. An apparatus according to claim 6 wherein the body tissue stimulating apparatus is a cardiac pacemaker.

11. An apparatus according to claim 10 wherein the cardiac pacemaker is a demand pacemaker.

12. In an implanted programmable cardiac pacer system having a select plurality of programmably alterable functions respectively controllable from an external programmer, said programmer coupling to said pacer a plurality of input signal bits respectively corresponding to said alterable functions, a security maintenance method for regulating said coupling, comprising the steps of:
 (a) detecting, at said implanted pacer, signal bits received at said programmer;
 (b) maintaining an iterative count of signal bits so received;
 (c) monitoring the accumulated time of said iterative count; and
 (d) enabling a programming change in said pacer only if said iterative count reaches and does not exceed a predetermined count during a predetermined accumulated time.

13. A method as described in claim 12 and further including the step of synchronizing said enabling step with the generation of pacing pulses by said pacer.

* * * * *